US012797425B2

(12) United States Patent
Lee et al.

(10) Patent No.: US 12,797,425 B2
(45) Date of Patent: Nov. 17, 2026

(54) COMPOSITION FOR PREVENTING OR TREATING MACULAR DEGENERATION CONTAINING GINSENG BERRY EXTRACT

(71) Applicant: HOLISTIC BIO CO., LTD., Seongnam-si (KR)

(72) Inventors: Sang Jun Lee, Seongnam-si (KR); Se Young Chung, Seoul (KR)

(73) Assignee: HOLISTIC BIO CO., LTD., Seongnam-si (KR)

( * ) Notice: Subject to any disclaimer, the term of this patent is extended or adjusted under 35 U.S.C. 154(b) by 455 days.

(21) Appl. No.: 18/270,687

(22) PCT Filed: Dec. 14, 2021

(86) PCT No.: PCT/KR2021/018975
§ 371 (c)(1),
(2) Date: Sep. 1, 2023

(87) PCT Pub. No.: WO2022/145813
PCT Pub. Date: Jul. 7, 2022

(65) Prior Publication Data

US 2024/0058408 A1 Feb. 22, 2024

(30) Foreign Application Priority Data

Dec. 30, 2020 (KR) ........................ 10-2020-0187943

(51) Int. Cl.
*A61K 36/258* (2006.01)
*A61K 31/704* (2006.01)
*A61P 27/02* (2006.01)

(52) U.S. Cl.
CPC .......... *A61K 36/258* (2013.01); *A61K 31/704* (2013.01); *A61P 27/02* (2018.01); *A61K 2236/331* (2013.01)

(58) Field of Classification Search
None
See application file for complete search history.

(56) References Cited

FOREIGN PATENT DOCUMENTS

| | | | |
|---|---|---|---|
| KR | 10-2011-0079564 | A | 7/2011 |
| KR | 10-2013-0044712 | A | 5/2013 |
| KR | 10-2014-0045260 | A | 4/2014 |
| KR | 10-2016-0026256 | A | 3/2016 |
| WO | 2020/238621 | A1 | 12/2020 |

*Primary Examiner* — Michael V Meller
(74) *Attorney, Agent, or Firm* — Bridgeway IP Law Group, PLLC; Jihun Kim

(57) ABSTRACT

A method for preventing or treating a macular degeneration disease, comprising administering a composition comprising a ginseng berry extract to a subject in need thereof. Since the composition can inhibit AE2 accumulation in retinal pigment epithelial cells, inhibit photooxidation, and inhibit outer nuclear layer damage of visual cells, it can be usefully used in preventing or treating macular degeneration disease.

5 Claims, 5 Drawing Sheets

COMPOSITION FOR PREVENTING OR TREATING MACULAR DEGENERATION CONTAINING GINSENG BERRY EXTRACT

BACKGROUND OF THE INVENTION

Field of the Invention

The present invention relates to a composition for preventing or treating macular degeneration disease, comprising a ginseng berry extract, and more particularly, a composition for preventing or treating macular degeneration disease, comprising a ginseng berry extract, wherein the ginseng berry extract is extracted by a water-soluble fractionation method to increase the content of ginsenoside Re as an active ingredient to be effective in inhibiting intracellular A2E accumulation, photooxidation, and outer nuclear layer damage of visual cells.

Description of the Related Art

Ginseng is one of the medicinal materials that have been traditionally used to treat various diseases in Asian countries such as China, Korea, and Japan. Ginseng saponin (ginsenoside), the main active ingredient of ginseng, is known to have various physiological activities, such as anti-aging activity, anti-inflammatory activity, antioxidant activity in the central nervous system, cardiovascular system, and immune system (Wu J Y, et al., J. Immunol., 148: 1519-25, 1992; Lee F C., Facts about ginseng, the elixir of life. Hollyn International. New Jersey, 1992; Huang K C., The pharmacology of Chinese herbs. CRC Press. Florida, 1999), antidiabetic activity (Chang H M., Pharmacology and application of Chinese material medica. Vol 1. World Scientific. Singapore, 1986), and antitumor activity (Sato K, et al., Biol. Pharm. Bull. 17:635-9, 1994; Mochizuki M, et al. al., Biol. Pharm. Bull. 18:1197-1202, 1995). To date, more than 30 ginsenosides have been isolated and identified from ginseng saponin, and Rb1, Rb2, Rc, and Rd, which are protopanaxadiol-based ginsenosides, and Re and Rg1, which are protopanaxatriol-based ginsenosides accounts for most of ginsenosides, which are glycosides comprising aglycone having a dammarane skeleton.

Meanwhile, ginsenoside is known to be metabolized by human intestinal microbes after being ingested, and the metabolites thereof have various physiological activities (Karikura M, et al., Chem. Pharm. Bull, 39:2357-61, 1991; Kanaoda M, et al., J. Tradit. Med. 11:241-5, 1994; Akao T, et al., Biol. Pharm. Bull. 21:245-9, 1998). For example, Rb1, Rb2, and Rc, which are protopanaxadiol-based saponins, are metabolized into 20-O-D-glucopyranosyl-20(S)-protopanaxadiol (IH-901, Compound K) (Hasegawa H, et al., Planta Medica 63:463-40, 1997; Tawab M A, et al., Drug Metab. Dispos. 31:1065-71, 2003), while Re and Rg1, protopanaxatriol-based ginsenosides saponins, are metabolized by intestinal bacteria into ginsenoside Rh1 or ginsenoside F1 (Hasegawa H, et al., Planta Medica 62:453-7, 1996; Tawab M A, et al., Drug Metab. Dispos. 31:1065-71, 2003). These converted compounds K, Rh1, and F1 exhibited various physiological activities. Specifically, Compound K is known to induce anti-metastatic or anti-cancer effects by blocking tumor invasion or preventing chromosome transformation and tumorigenesis (Wakabayashi C, et al., Oncol. Res. 9:411-7, 1998; Lee S J, et al., Cancer Lett. 144:39-43, 1999), and Rh1 has a cytotoxic effect against the growth of various cancer cells (Odashima S, et al., Cancer Res. 45:2781-4, 1985; Ota T, et al., Cancer Res. 47:3863-7, 1987; Lee H Y, et al., Differentiation mechanism of ginsenosides in cultured murine F9 teratocarcinoma stem cells. Proc. 6th Int. Ginseng symp. Seoul 127-31, 1993) as well as anti-allergic and anti-inflammatory activities (Park E K, et al., Int. Arch. Allergy Immunol. 133:113-120, 2004). In addition, F1 is known to be capable of significantly reducing UV-B-induced cell death and downregulating the expression of Bcl-2 and Brn-3a to protect human HaCaT keratinocytes from apoptosis by UV-B irradiation (Lee E H, et al., J. Invest. Dermatol. 121:607-13, 2003).

The nerve tissue located in the center of the inner retina of the eye is referred to as macula, and most of the visual cells are gathered here. In addition, the place where the image of an object is formed is also the center of the macula. Therefore, the macula plays a critical role in vision. Visual acuity refers to the ability to recognize the existence and shape of an object, wherein it is most sensitive when the image of an object is focused on the fovea of the macula (central visual acuity), and it is decreased towards the periphery of the retina (peripheral visual acuity). When an object is viewed, the object is viewed through the central part of the retina, which is the macula, and so the central visual acuity is generally referred to as visual acuity. The macula may cause visual impairment due to various causes such as aging, genetic factors, toxicity, and inflammation, and the visual impairment is referred to as macular degeneration.

Macular degeneration affects central visual acuity, making the center of the field of vision blurry, and may make it difficult to perform sophisticated activities such as reading and driving through the through central scotoma, metamorphosis, or local vision loss. Macular degeneration is a very serious disease that may lead to blindness in severe cases.

The underlying mechanism of macular degeneration is still unknown. Senile macular degeneration, which is a type of macular degeneration, is characterized by loss of central visual acuity due to the death of photoreceptor cells, and is considered as having a multifactorial etiological mechanism. Recently, it has been reported that various factors (e.g., smoking, obesity, dietary habits, increased blood cholesterol level, blue light irradiation, etc.) cause the acceleration of senile macular degeneration, in which degeneration (deterioration) of the retinal pigment epithelium is caused by the damage of photoreceptor cells and the cell death thereby.

In addition, it is known that the accumulation of lipofuscin in the center of the eye retina is greatest in the retinal pigment epithelial cells below the center of the retina. This reflects the fact that many rod cell photoreceptors are concentrated in this area. N-retinyl-N-retinylidene ethanolamine (A2E), which is a major chromophore of lipofuscin, induces the production of reactive oxygen species when exposed to blue light. Blue light has relatively high energy of about 440 nm, and when exposed thereto for a short time, cell damage increases, and this increases is more when exposed to light of a shorter wavelength. Therefore, continuous light exposure further accelerates the death of retinal pigment epithelial cells in senile macular degeneration, which eventually becomes one of the main causes of degeneration of photoreceptor cells.

In addition, decrease of visual acuity due to retinal cell dysfunction is closely related to A2E oxidation, and thus it may be a major cause of senile macular degeneration.

However, treatments available for this type of macular degeneration are very rare to date. Moreover, there are some treatments such as anti-VEGF for wet macular degeneration, but there is no known treatment for dry macular degeneration.

Korean Patent Publication No. 2014-0045260 discloses a composition for preventing and treating reduced eye function and macular degeneration disease through retinal regeneration by a ginseng extract. However, in the patent above, the ginseng extract is extracted by selecting one or more of water, ethanol, methanol, and butanol as a solvent. Generally, however, a ginseng extract extracted from the root contains about 5 times less ginsenoside content than the ginseng berry.

In this background, it is necessary to perform research and development on a ginseng berry extract or fractionated extract with significantly increased content of active ingredients and marker ingredients of ginseng berries compared to an extract extracted by the general ginseng root extraction methods. In addition, there is a need to develop a therapeutic agent capable of treating or preventing macular degeneration disease.

SUMMARY OF THE INVENTION

The technical task to be accomplished by the present invention is to provide a composition for preventing or treating macular degeneration disease, comprising a ginseng berry extract, wherein the ginseng berry extract is extracted by a water-soluble fractionation method to increase the content of ginsenoside Re as an active ingredient to be effective in inhibiting intracellular A2E accumulation, photooxidation, and outer nuclear layer damage of visual cells.

The technical task to be accomplished by the present invention is not limited to the abovementioned technical task, and other technical tasks that are not mentioned may be clearly understood by those skilled in the art from the description below.

To accomplish the technical task above, one embodiment of the present invention provides a pharmaceutical composition for preventing or treating macular degeneration disease comprising a ginseng berry extract.

To accomplish the technical task above, another embodiment of the present invention provides a food composition for preventing or treating macular degeneration disease comprising a ginseng berry extract.

According to an embodiment of the present invention, a ginseng berry extract obtained by extracting ginseng berries by a water-soluble fractionation method has a higher ginsenoside content, including ginsenoside Re, than a ginseng root extract, comprises various active ingredients that are not present in the root, such as polycenol (syringaresinol, anthocyanin, etc.), and exhibits a significant effect in preventing, treating or ameliorating eye diseases, especially macular degeneration disease, by inhibiting intracellular A2E accumulation, photooxidation, and outer nuclear layer damage of visual cells.

The effects of the present invention are not limited to the effects described above, and should be understood as including all effects that may be inferred from the description of the present invention or the features of the invention described in the claims.

DETAILED DESCRIPTION OF THE EMBODIMENTS

Figure 1:
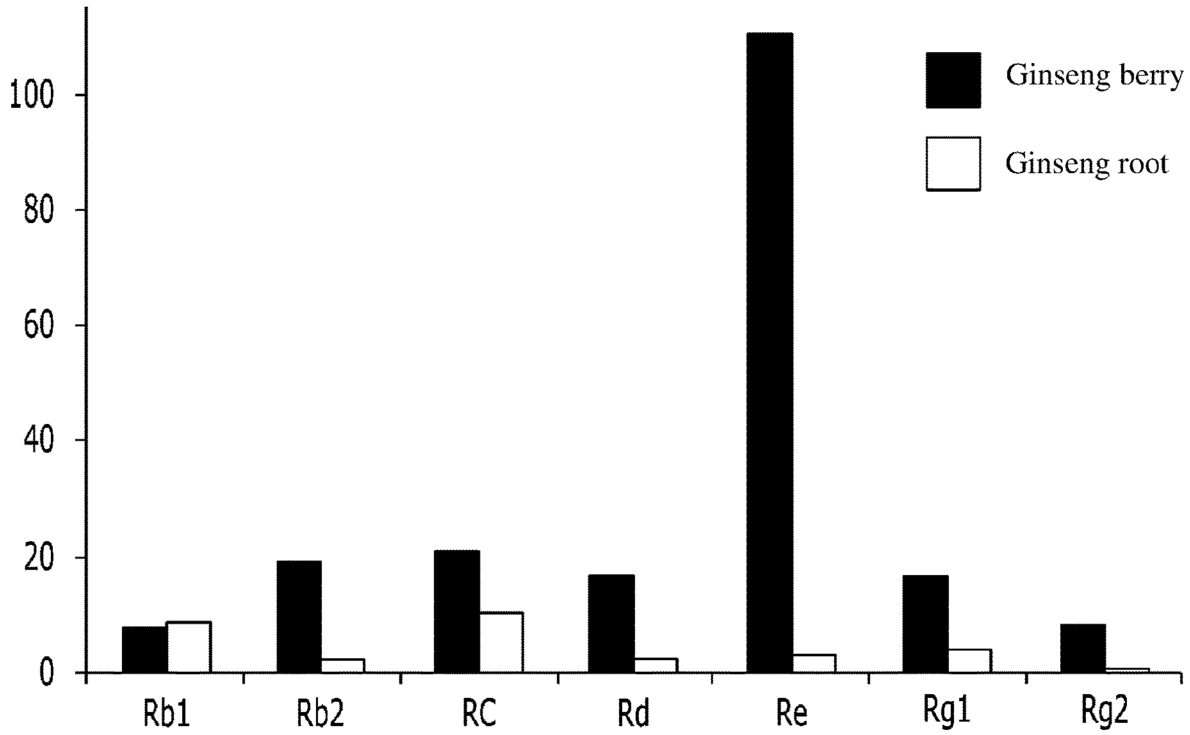
FIG. 1 is a graph showing the results of analyzing the ginsenoside ingredients of a ginseng berry extract and those of a ginseng root extract as a comparative example.

The present invention provides a pharmaceutical composition for preventing or treating macular degeneration disease comprising a ginseng (*Panax ginseng*) berry extract as an active ingredient.

Ginseng (*Panax ginseng*), which is a plant belonging to the *Panax* genus of the Araliaceae family, is a unique medicinal plant of South Korea, the country of origin, and has been widely used for 2,000 years. The ginseng is composed of a root, leaves, stem, berry, and flower. As the ginseng, one selected from the group consisting of *Panax ginseng, P. quiquefolius, P. notoginseng, P. japonicus, P. trifolium, P. pseudoginseng, P. vietnamensis, Panax quinquefolium*, and a combination thereof may be used, but it is not limited thereto. Preferably, the ginseng used in the present invention is *Panax ginseng*.

A ginseng berry is a part of ginseng, and it contains different types of ingredients and has a different content composition from the commonly used ginseng root.

Specifically, ginseng berries contain more vitamins and minerals than ginseng roots. In addition, ginseng berries contain more ginsenosides than ginseng roots, and the composition of the ginsenosides contained is different. Therefore, in one embodiment of the present invention, a ginseng berry extract may contain ginsenosides PT (protopanaxatriol), including Re, Rg1, and Rg2, more than ginsenosides PD (protopanaxadiol), including Rb1, Rb2, Rc, and Rd, and thus it may exhibit a different effect. For example, it was recently reported that ginseng berries exhibited better antidiabetic efficacy than ginseng root (Dey L. et al., Phytomedicine, 10; 600-605, 2003).

In addition, as ginseng berries become overripe from green color, like that of their leaves, the flesh turns to red or yellow depending on the variety. As the color of the flesh changes, anthocyanins are formed in ginseng berries. Anthocyanins include, for example, cyanidin chloride, delphinidin chloride, malvidin chloride, pelargonin chloride, cyanin chloride, ideain chloride, keracyanin chloride, kuromanin chloride, pelagonidin chloride, and petunidin chloride (Nat. Prod. REP., 2009, 26, 1001-1043). In addition, it has been reported that anthocyanins have antioxidant, anti-allergic, anti-inflammatory, antiviral, antiproliferative, antimutagenic, antibacterial, and anticarcinogenic effects, and are effective in the protection from cardiovascular damage and allergy, protection of microcirculation, protection of peripheral capillary resistance, and the amelioration of diabetes and the like (Asia Pac J Clin Nutr. 2007; 16(2):200-8).

Therefore, since a ginseng berry extract may abundantly contain vitamins, minerals, ginsenosides, anthocyanins, and the like as described above, the composition according to one embodiment of the present invention may promote the overall health of eyes by ameliorating eye fatigue, dryness, and the like.

In addition, the ginseng berry extract may be prepared by a preparation method comprising the following steps:

1) preparing an extract by adding an extraction solvent to ginseng berries;
2) filtering the extract of Step 1);
3) subjecting a filtrate filtered in Step 2) to reduced pressure concentration and then drying the same.

In the method described above, the ginseng berries of Step 1) may be used without limitation, such as cultivated ones and commercially available ones.

In the method described above, the ginseng berries may comprise the pericarp (everything else except the seed of the berries) or seeds of the ginseng berries, and may specifically be the pericarp of the ginseng berries.

In addition, the extraction solvent of Step 1) may be water. The extraction solvent may be added in an amount of 1 to 10 mL per 1 g of the weight of the ginseng berries used for extraction, and specifically, in an amount of 1 to 5 mL.

The method of extraction of Step 1) may be shaking extraction, Soxhlet extraction, reflux extraction, or ultrasonic extraction. In one embodiment of the present invention, the method of extraction may be ultrasonic extraction. At this time, the extraction temperature may be 15 to 45° C., specifically 15 to 35° C., more specifically 20 to 30° C. In addition, the extraction pressure may be 200 to 1,000 MPa, specifically 300 to 900 MPa, and more specifically 400 to 800 MPa. The extraction time may be 10 seconds to 1 hour, specifically 20 seconds to 30 minutes, and more specifically 30 seconds to 5 minutes. In addition, the number of times of extraction may be 1 to 5 times, specifically 1 to 3 times. In a range out of the conditions of the extraction temperature, extraction pressure, extraction time, or number of times of extraction, the content of the active ingredient in the ginseng berry extract may be insignificant, because extraction is not sufficiently carried out. Alternatively, the efficiency of the extraction operation may decrease because the extraction yield is no longer increased.

The reduced pressure concentration in Step 3) may be performed by using a rotary vacuum evaporator or rotary evaporator. In addition, the drying may be reduced pressure drying, vacuum drying, boiling drying, spray drying or freeze drying.

The ginseng or ginseng berry extract according to the present invention is as described above. In one embodiment of the present invention, the ginseng berry may be any one selected from the group consisting of seeds, berries, immature berries, mature berries, flesh, and pericarp of ginseng, and combinations thereof, and preferably it may be flesh, but is not limited thereto.

"Extract" mentioned in the present invention means a substance extracted from a raw material by any method, and is used in the sense of including all of an extract obtained thereby, a concentrate obtained therefrom, and a dried product and a powder of the concentrate without limitation.

The extract may be obtained by extracting from a raw material or a dried product thereof, and a raw material of the extract may be used without limitation, such as cultivated one or commercially available one.

When the extract is obtained by extraction from a raw material, all known conventional extraction methods such as solvent extraction, ultrasonic extraction, filtration, and reflux extraction may be used as an extraction method, and preferably the extract may be prepared by using solvent extraction or reflux extraction. The extraction process may be repeated several times, and then additional steps such as concentration or freeze-drying may be performed. Specifically, an obtained extract may be concentrated under reduced pressure to obtain a concentrate, and the concentrate may be freeze-dried, and then a grinder may be used to prepare a high-concentration extract powder. The extract also comprises fractions obtained by further fractionating the extract.

The extract may be extracted by using water as an extraction solvent. When extracting ginseng, the amount of solvent added may be 5 to 20 times, preferably 7 to 18 times, and more preferably 9 to 16 times the weight of 500 g of herbal medicine, but is not limited thereto. When extracting ginseng berries, the amount of solvent added may be 10 to 30 times, preferably 13 to 27 times, and more preferably 15 to 25 times the weight of 1000 g of herbal medicine, but is not limited thereto. Extraction may be carried out at 60° C. to 100° C., preferably at 65° C. to 95° C., more preferably at 70° C. to 90° C., but is not limited thereto. Extraction may be carried out for 4 hours to 20 hours, preferably for 4 hours to 16 hours, and more preferably for 4 hours to 12 hours, but is not limited thereto. Extraction may be performed 1 to 8 times, preferably 1 to 6 times, and more preferably 1 to 5 times, but is not limited thereto. The extract may be a single extract obtained from each extraction or a mixed extract of extracts obtained from each extraction. Among the extraction conditions, when the amount and temperature of the solvent added during extraction and time are less than the lower limits or when the number of times of extraction exceeds the upper limit, macular degeneration disease may not be ameliorated even if a ginseng extract and a ginseng berry extract are mixed.

The ginseng berry extract may contain ginsenoside Re. When the ginseng berry was extracted with 100% water, the LS-MS measurement results may confirm that various ginsenosides are included, such as ginsenoside Re, malonyl-ginsenoside Re, notoginsenoside R3, ginsenoside Rg1, ginsenoside R2, and ginsenoside Rd. In particular, because ginsenoside Re is present the most, the main efficacy of the ginseng berry extract may be due to ginsenoside Re.

According to one embodiment of the present invention, the composition may increase SIRT 1 (Sirtuin 1) expression and mitochondrial synthesis of retinal cells.

The SIRT 1 (Sirtuin 1), an $NAD^+$-dependent histone protein deacetylase, is known to normalize mitochondrial functions by enhancing mitochondrial biosynthesis in muscles and the like, thus increasing the proportion of mitochondria containing stable DNA in cells and further inhibiting the aging of cells. In particular, in the case of the retinal degeneration transgenic mouse model, it is known that SIRT 1, which is expressed in cells present in the retina, such as retinal ganglion cells, inner retinal cells, photoreceptor cells, and retinal pigment epithelial cells, is present in non-ideal locations within retinal cells, and exhibits accelerated cell death. Therefore, a substance that enhances the expression of SIRT 1 may enhance the biosynthesis of mitochondria in retinal cells to normalize their functions and inhibit the instability of mitochondrial DNA to reduce cell damage and death, thereby preventing and ameliorating eye diseases including macular degeneration.

In addition, according to one embodiment of the present invention, the composition preferably has one or more effects selected from the group consisting of inhibition of AE2 accumulation in retinal pigment epithelial cells, inhibition of death of retinal pigment epithelial cells induced by blue light, and inhibition of damage to the outer nuclear layer of visual cells, but the effect is not limited thereto.

The pharmaceutical composition of the present invention may comprise a pharmaceutically acceptable carrier or diluent, and may each be formulated according to conventional methods in the form of oral formulations, such as powder, granule, tablet, capsule, suspension, emulsion, syrup, and aerosol, external preparations, suppositories, and sterile injectable solutions. The pharmaceutically acceptable carrier comprises lactose, dextrose, sucrose, sorbitol, mannitol, xylitol, erythritol, maltitol, starch, gum acacia, alginate, gelatin, calcium phosphate, calcium silicate, cellulose, methylcellulose, microcrystalline cellulose, polyvinyl pyrrolidone, water, methylhydroxybenzoate, propylhydroxybenzoate, talc, magnesium stearate, mineral oil, and the like. In addition, diluents or excipients such as fillers, extenders, binders, wetting agents, disintegrants, and surfactants are included. Oral solid preparations include tablets, pills, powders, granules, capsules, and the like. These solid preparations may contain at least one excipients, for example, starch, calcium carbonate, sucrose or lactose, gelatin, and the like, and may include lubricants such as magnesium stearate and talc. Oral liquid preparations may include suspensions, internal solutions, emulsions, syrups, and the like, and may include diluents such as water and liquid paraffin, wetting agents, sweeteners, aromatics, preservatives, and the like. Parenteral preparations include sterilized aqueous solutions, non-aqueous solvents, suspensions, emulsions, creams, lyophilized preparations, and suppositories, and non-aqueous solvents and suspensions include propylene glycol, polyethylene glycol, vegetable oils such as olive oil, and injectable esters such as ethyl oleate. As a base for the suppository, Witepsol, Macrogol, Tween 61, cacao butter, laurin butter, glycerogelatin, and the like may be used.

The dose of the active ingredient contained in the pharmaceutical composition of the present invention varies depending on the conditions and the weight of the patient, the severity of the disease, the type of the active ingredient, and the administration route and period, and may be appropriately adjusted according to the patient. For example, the active ingredient may be administered at a dose of 0.0001 to 1000 mg/kg per day, preferably 0.01 to 100 mg/kg, and the administration may be carried out once or several times a day. In addition, the pharmaceutical composition of the present invention may comprise the active ingredient in an amount of 0.001 to 90% by weight based on the total weight of the composition.

The pharmaceutical composition of the present invention is administered to mammals such as rats, mice, livestock, and humans through various routes, for example, oral, dermal, abdominal, rectal administration, or intravenous, intramuscular, subcutaneous, intrauterine intrathecal or intracerebroventricular injection.

According to one embodiment of the present invention, a food composition for preventing or treating macular degeneration disease comprising a ginseng berry extract is provided. Details of the ginseng berry extract are as described above.

In addition, according to one embodiment of the present invention, the food composition may be extracted by selecting water as a solvent, and the specific details are as described above.

In addition, according to one embodiment of the present invention, as mentioned above, the food composition may increase SIRT 1 (Sirtuin 1) expression and mitochondrial synthesis of retinal cells.

In addition, according to one embodiment of the present invention, the food composition may have one or more effects selected from the group consisting of inhibition of AE2 accumulation in retinal pigment epithelial cells, inhibition of death of retinal pigment epithelial cells induced by blue light, and inhibition of damage to the outer nuclear layer of visual cells. The content related thereto is the same as that described in "Pharmaceutical composition for preventing or treating macular degeneration disease", and so the description thereof is omitted.

For the food composition according to one embodiment of the present invention, there is no particular limitation on the type of food. The type of food may be, for example, meat, sausage, bread, chocolate, candy, snacks, confectionery, pizza, ramen, gums, dairy products, various soups, beverage, tea, drink, alcoholic beverage, vitamin composite, and the like, and may include all foods in a conventional sense.

In addition, the food composition may be added to food or beverage for the purpose of preventing or treating macular degeneration disease. At this time, the amount of the ginseng berry extract added in the food or beverage may be 0.01 to 15% by weight of the total weight of the food, and a health drink composition may be added at a ratio of 0.02 to 5 g, preferably 0.3 to 1 g based on 100 ml.

The health functional beverage composition of the present invention is not particularly limited in other ingredients except for containing the composition containing the ginseng berry extract as essential ingredients in the indicated ratios, and may contain additional ingredients such as various flavoring agents or natural carbohydrates as in conventional beverages. Examples of the natural carbohydrates described above are monosaccharides such as glucose, fructose, and the like; disaccharides such as maltose, sucrose and the like; and polysaccharides such as conventional sugars including dextrins, cyclodextrins, and the like; and sugar alcohols such as xylitol, sorbitol, and erythritol. As flavoring agents other than those described above, natural flavoring agents such as thaumatin and *stevia* extracts, for example, rebaudioside A and glycyrrhizin; and synthetic flavoring agents such as saccharin, aspartame, and the like may be advantageously used. The proportion of the natural carbohydrates is generally about 1 to 20 g, preferably about 5 to 12 g per 100 ml of the composition of the present invention.

In addition to those described above, the composition containing the ginseng berry extract of the present invention may contain various nutrients, vitamins, minerals (electrolytes), synthetic and natural flavoring agents, colorants and enhancers (cheese, chocolate, etc.), pectic acid and salts thereof, alginic acid and salts thereof, organic acids, protective colloidal thickeners, pH adjusting agents, stabilizers, preservatives, glycerin, alcohol, carbonating agents used in carbonated beverages, and the like. In addition, other compositions containing the ginseng berry extract of the present invention may contain natural fruit juice and fruit flesh for producing fruit juice beverage and vegetable beverage. These ingredients may be used either independently or in combination. At this time, the ratio of the additive is not very important, but it is generally selected in a range of 0 to about 20 parts by weight per 100 parts by weight of the composition containing the ginseng berry extract of the present invention.

The food composition according to one embodiment of the present invention can be applied to not only animals but also humans.

Hereinafter, the present invention will be described in more detail through Examples and Test Examples. However, the following Examples and Test Examples are intended to illustrate the present invention, and the scope of the present invention is not limited thereto.

Example 1

Ginseng berries 100 g harvested from 4-year-old or older ginseng were washed, and the washed ginseng berries were put into a seed separator with about 3 times as much purified water and subjected to a separation process to obtain the pericarp of the ginseng berries excluding the seeds. The obtained product including the pericarp was subjected to ultra-high pressure treatment at room temperature (around 25° C.) for 1 minute at a pressure of 600 MPa, and then a ginseng berry extract was obtained by using a general press.

Example 2

Confirmation of Ginsenoside Re and Syringarecinol Ingredients of Ginseng Berry Extract (1) Sample Extraction and Reaction Each ground GB sample 600 mg was extracted with 6 mL of 70% methanol by using a Retsch MM400 mixer mill (Retsch GmbH, Haan, Germany) operated at 30 Hz/s for 10 minutes.

Thereafter, the sample was ultrasonicated for 5 minutes in an ultrasonic water bath (Power Sonic 305; Hwashin Technology Co., Ltd., Seoul) and centrifuged at 17000 rpm for 15 minutes at 4° C.

The supernatant was filtered by using a 0.2 mm polytetrafluoroethylene filter and concentrated by using a speed vacuum concentrator (Modulspin 31; Biotron, Incheon, Korea).

The finally collected sample was weighed and reconstituted in 70% methanol. The finally obtained concentration of the sample was 50 mg/ml for ultrahigh-performance liquid chromatography-electrospray ionization-tandem mass spectrometry (UHPLC-ESI-MS/MS) analysis.

(2) UHPLC-ESI-MS/MS Analysis

The analysis was performed by using LTQ XL ion trap mass spectrometer (Dionex Corporation, Sunnyvale, CA, USA) having an electrospray interface combined with a Dionex UltiMate 3000 RS pump, an RS autosampler, an RS column compartment, and an RS diode array detector (Dionex Corporation, Sunnyvale, CA, USA).

A sample with an injection volume of 10 mL was separated on a Thermo Scientific Syncronis C18 UHPLC column (100 mm, 2.1 mm [i.d.] 1.7 mm [particle size], Thermo Fisher Scientific, San Jose, CA, USA) at a constant flow rate of 3 mL/min.

A gradient mobile phase consisted of solvent A (water+0.1% formic acid) and solvent B (acetonitrile+0.1% formic acid). The LC gradient was increased from 10% solvent B to 100% solvent B in 15 minutes, held for 3 minutes, and then re-equilibrated to the initial conditions within 4 minutes.

A photodiode array detector was adjusted to a wavelength range of 200 to 600 nm for metabolite detection managed by a three-dimensional field. The instrument was operated in a full scan mode with a mass scan range of 150 to 1500 m/z.

The operating parameters were capillary temperature of 270° C. and a sheath gas flow and an auxiliary gas flow of 40 and 20 AU, respectively.

Cation (and anion) mode conditions for ESI were capillary voltage of 45 kV (31 kV), source voltage of 5 V (4.5 V), and tube lens voltage of 120 V (60 V).

Figure 2:
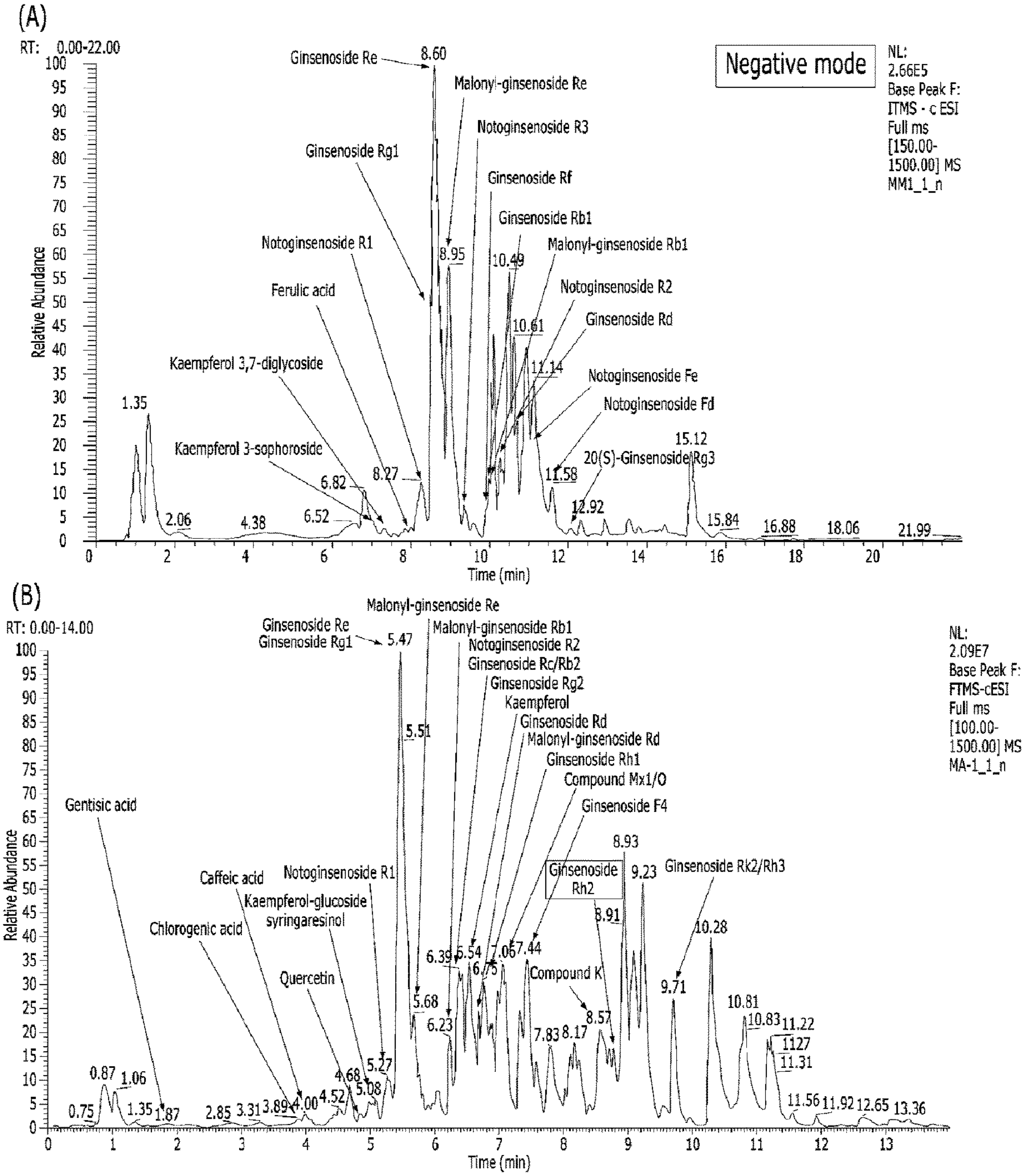
FIG. 2 is (A) a graph showing the results of LC-MS chromatogram analysis of a 100% water extract of ginseng berries, and (B) a graph showing the results of LC-MS chromatogram obtained by extracting with alcohol a ginseng berry sludge remaining after extracting ginseng barriers into the 100% water extract.

FIG. 2(A) show the results of the LC-MC chromatogram analysis of a 100% water ginseng berry extract. As shown in FIG. 2(A), most of the ginsenosides were ginsenosides found in ginseng, and there were various ginsenosides such as ginsenoside Re, ginsenoside Rf, and ginsenoside Rd, among which ginsenoside Re was found to be the most abundant. It was confirmed that syringarecinol was not present in the 100% water ginseng berry extract.

FIG. 2(B) shows the results of the LC-MC chromatogram analysis of an alcohol extract of the ginseng berry sludge that was left after extracting ginseng berries with 100% water.

The EtOH extract was concentrated and subjected to Sephadex LH-20 column chromatography by using 50% aqueous methanol. As a result, 8 fractions were obtained, and most of the syringarecinol contained in ginseng berries was obtained from the 6th fraction which exhibited strong SIRT1 activity through bioassay guided fractionation. It was analyzed and finally confirmed in the LC-MS chromatogram.

It was confirmed that the syringarecinol ingredient, which was almost absent in the water extract, was dissolved into the 50% ethanol extract.

Therefore, it was confirmed that the SIRT activity of the 100% water ginseng berry extract was from other ginsenosides including ginsenoside Re, and that the main active ingredient was ginsenoside Re.

Example 3

Confirmation of Toxicity of Ginseng Berry Extract to ARPE-19 Cells

An experiment was performed to confirm a cytotoxicity-free concentration. Human retinal pigment epithelial cells (ARPE-19, ATCC) were aliquoted in a 96-well tissue culture plate at a density of $1\times10^4$ cells/well and cultured for 24 hours. The cells were treated with the ginseng berry extract at different concentrations (12.5, 25, 50, 100, 200, 400, 800 μg/mL), and the cell viability was measured 24 hours later by using Cell Count Kit-8 (Dojindo Labs, Japan).

Figure 3:
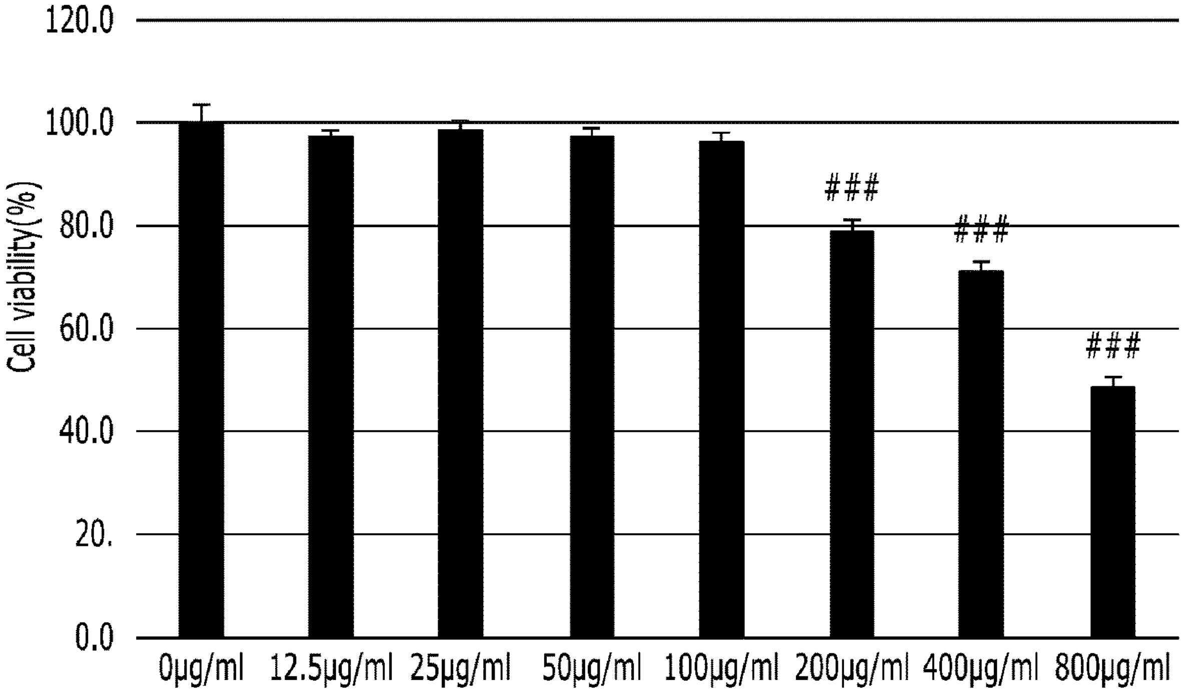
FIG. 3 is the results of confirming the concentration exhibiting cytotoxicity when a ginseng berry extract is treated with retinal pigment epithelial cells (ARPE-19).

The experimental results are shown in FIG. 3. As shown in FIG. 3, when the ARPE-19 cells were cultured and the cell viability was measured after treating the ginseng berry extract, cytotoxicity was found from a concentration of 200 μg/mL.

Example 4

Confirmation of the Effect of Ginseng Berry Extract for Inhibiting ARPE-19 Cell Death by Blue Light An experiment described below was performed regarding the preventive effect of the ginseng berry extract against ARPE-19 cell death due to A2E.

ARPE-19 cells, which are cells without any A2E therein, were used, and the cells were cultured in a medium of DMEM containing 10% FBS, 100 μm/ml penicillin, and 100 mg/mL streptomycin under humid conditions of 5% CO2 at 37° C.

The human retinal pigment epithelial cells (ARPE-19 cells) were aliquoted in a 96-well tissue culture plate at a density of $1\times10^4$ cells/well and cultured for 24 hours. Then, as an experimental group, before A2E accumulation in the cultured ARPE-19 cells, a ginseng berry extract (25, 50, and 100 μg/mL) was treated, respectively. After 24 hours, A2E dissolved in DMEM at 20 μM was treated to accumulate A2E in the ARPE-19 cells. As a positive control group, 30 μM of lutein instead of the ginseng berry extract was treated before A2E accumulation, and A2E was accumulated in a negative control group without preliminary drug treatment.

After treating with A2E and culturing for 24 hours, blue light (BL, 430 nm, 6000 lux) was irradiated for 20 minutes, and after 24 hours, cell viability was measured by using a cell count kit.

To investigate the photooxidation by blue light induction (post-treatment), ARPE-19 cells were seeded to a 96-well plate at $1\times10^4$ cell/well and then incubated→(24 hr later) A2E (20 μM) pre-treated once→(after 24 hr) post-treated with a ginseng berry extract (25, 50, 100 μg/ml) once→(after 24 hr) irradiated with blue light (6000 lux, 20 min)→and then, (after 24 hr) the cell viability was measured by using the cell count kit.

Figure 4:
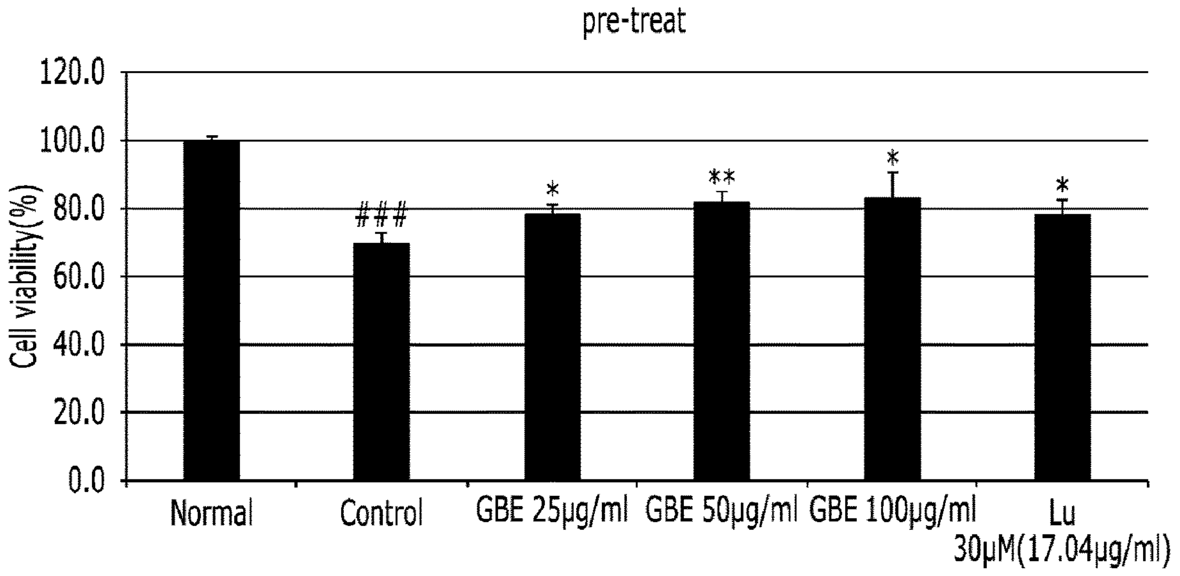
FIG. 4 shows an inhibitory effect of a ginseng berry extract on ARPE-19 cell death caused by blue light.

FIG. 4 shows the experimental results. As shown in FIG. 4, cell death caused by blue light irradiation was reduced by the treatment with the ginseng berry extract. Compared to the normal group, the cell viability was 69.82% in the negative control group, and the expression levels were 78.24%, 81.83%, and 83.02% in the groups treated with 25, 50, and 100 μg/ml of the ginseng berry extract, respectively. The cell viability in the lutein treatment group, the positive control group, was 78.31%.

Therefore, the cell viability was decreased by about 30.2% in the negative control group compared to the normal group, and the recovery rates were 27.9%, 39.8%, and 43.7% in the experimental groups treated with 25, 50, and 100 μg/ml of the ginseng berry extract, respectively, compared to the negative control group. The cell viability was significantly increased at 25, 50, and 100 μg/ml.

The experiment described above showed that the treatment with the ginseng berry extract had an effect of inhibiting ARPE-19 cell depth due to blue light.

Example 5

Measurement of Cell Protection Capability and Cell Viability Against Blue Light-Induced Photooxidation Since the A2E accumulated in human retinal pigment epithelial cells (ARPE-19 cells) is known to induce cytotoxicity when irradiated with blue light (BL), cell protective capability and cell viability against blue light-induced photooxidation were analyzed.

Human retinal pigment epithelial cells (ARPE-19 cells) were aliquoted in a 96-well tissue culture plate at a density of $1\times10^4$ cells/well and cultured for 24 hours. After treating with A2E at a concentration of 20 μM and culturing for 24 hours, the experimental group was treated with 25, 50, and 100 μg/mL of the ginseng berry extract, a positive control group was treated with 30 μM of lutein instead of the ginseng berry extract, and A2E was accumulated in a negative control group without preliminary drug treatment. After culturing for 24 hours, blue light (BL, 430 nm, 6000 lux) was irradiated for 20 minutes, and after 24 hours, the cell viability was measured by using the cell count kit.

Figure 5:
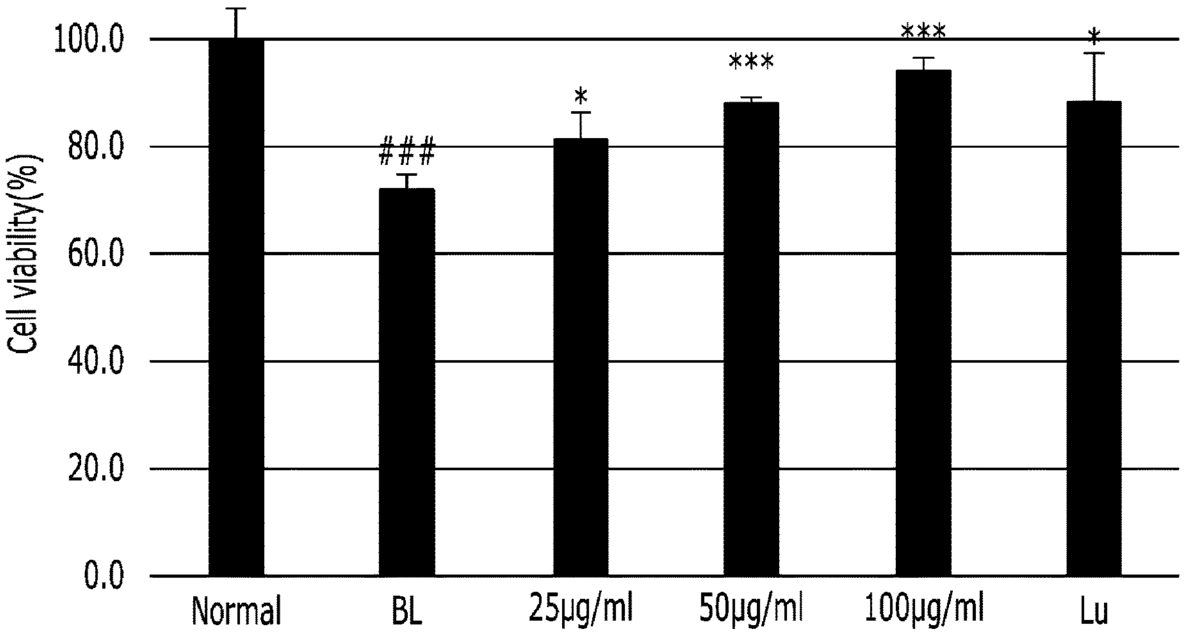
FIG. 5 shows the photooxidative protection effect of a ginseng berry extract against A2E caused by blue light in ARPE-19 cells.

The experimental results are shown in FIG. 5.

As shown in FIG. 5, the cell death due to photooxidation of A2E caused by blue light irradiation was reduced by the treatment with the ginseng berry extract. The cell viability was 72.04% in the negative control group compared to the normal group, and the expression levels were 81.43%, 87.83%, and 93.69% in the groups treated with 25, 50, and 100 μg/ml of the ginseng berry extract, respectively. The cell viability in the lutein treatment group, the positive control group, was 88.19%.

Therefore, the cell viability was decreased by about 28.0% in the negative control group compared to the normal group, and the recovery rates were 33.6%, 56.5%, and 77.4% in the experimental groups treated with 25, 50, and 100 μg/ml of the ginseng berry extract, respectively, compared to the negative control group. The cell viability was significantly increased at 25, 50, and 100 μg/ml.

The experiment described above showed that the treatment with the ginseng berry extract had an effect of inhibiting cell depth due to blue light-induced photooxidation.

Example 6

Confirmation of Treatment Effect in Blue Light-Induced Macular Degeneration Animal Model Balb/C mice (purchased from DBL) were acclimatized for one week, then the ginseng berry extract was administered once a day for 5 days. After dark adaptation for 24 hours, blue light was irradiated at 10,000 lux for 1 hour per day for 2 weeks (14 days). The test substance was administered once a day, and then 24 hours later, autopsy was performed to extract the eyeball including the optic nerve. The extracted ocular tissues were fixed in the Davidson solution for 10 days, and then fixed in formalin for 1 to 2 days. Thereafter, paraffin blocks were prepared and H&E staining was performed.

The stained ocular tissue was observed to confirm the thickness of the outer nuclear layer, inner nuclear layer, photoreceptor layer, and the whole retina of visual cells.

Figure 6:
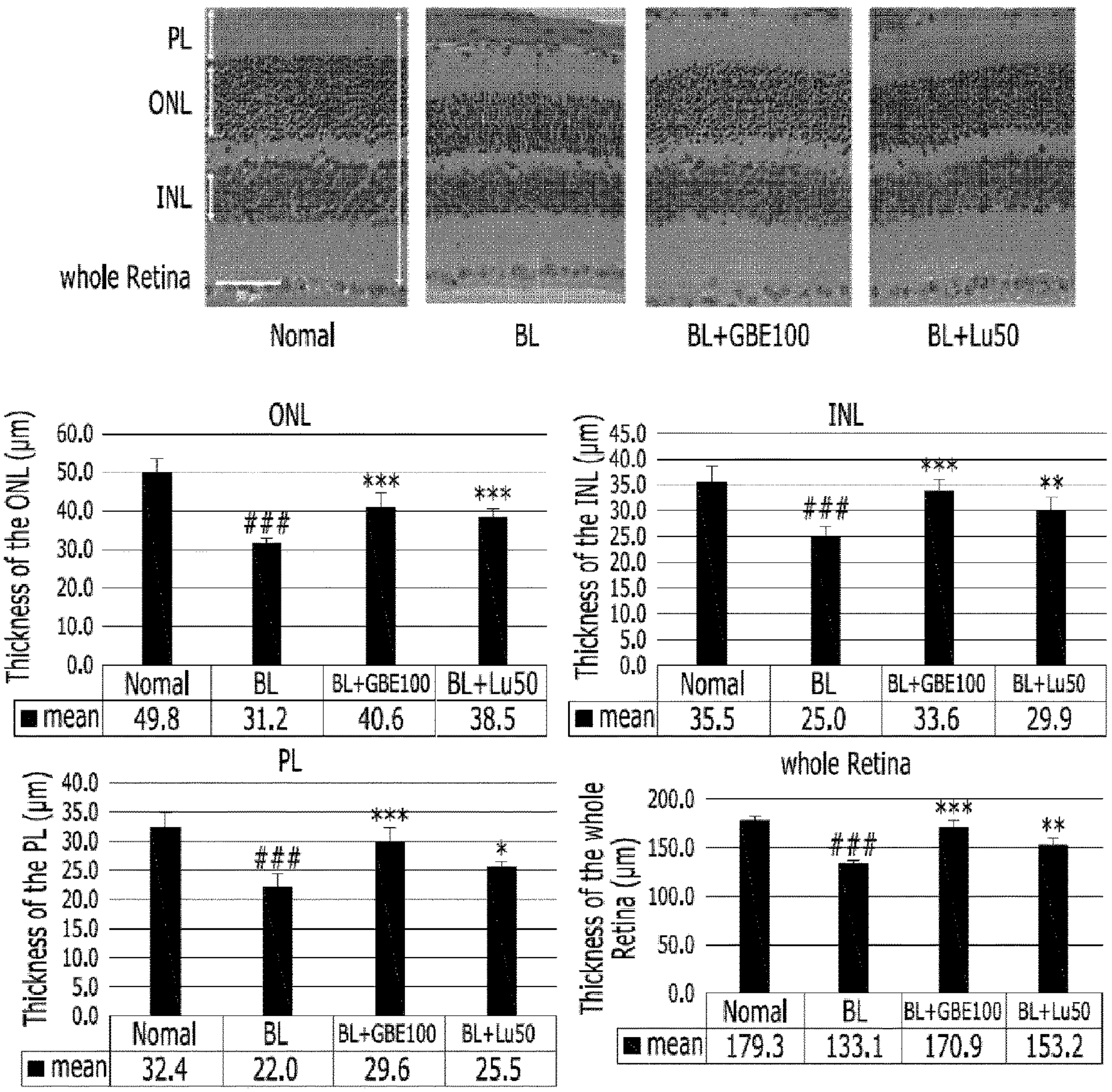
FIG. 6 shows the results of confirming the inhibition of retinal visual cell layer damage according to the administration of a ginseng berry extract to an animal model of macular degeneration induced by blue light (ONL: outer nuclear layer; INL: inner nuclear layer; PL: photoreceptor segment layer PL, and whole retina).

The analytical results are shown in FIG. 6. Referring to FIG. 6, when 100 mg/kg of the ginseng berry extract was administered, the outer nuclear layer (ONL) showed a recovery rate of 50.4% compared to the blue light irradiation group, which was a negative control group. The inner nuclear layer (INL) showed a recovery rate of 82.8%, the photoreceptor segment layer (PL) 73.3%, and the whole retina 81.8%.

Therefore, it was confirmed that damage to the retinal layer was restored when the ginseng berry extract was administered at 100 mg/kg.

The description of the present invention above is for illustrative purposes, and those skilled in the art can understand that it can be easily modified into other specific forms without changing the technical principles or essential features of the present invention. Therefore, the embodiments described above should be understood as illustrative in all respects and not limiting. For example, each component described as a single type may be implemented in a distributed manner, and similarly, components described as distributed may be implemented in a combined form.

The scope of the present invention is indicated by the claims described below, and all changes or modifications derived from the meaning and scope of the claims and equivalent concepts thereof should be interpreted as being included in the scope of the present invention.

MODES FOR CARRYING OUT THE INVENTION

Modes for carrying out the invention have been described together in the best mode for carrying out the invention.

INDUSTRIAL APPLICABILITY

The composition containing the ginseng berry extract according to an embodiment of the present invention inhibits A2E accumulation in retinal pigment epithelial cells and inhibits photooxidation and outer nuclear layer damage of visual cells, and thus can be used as a therapeutic agent of eye diseases, particularly, macular degeneration disease and used in health functional food industry.

What is claimed is:

1. A method for treating macular degeneration in a human in need thereof comprising administering a therapeutically effective amount of a ginseng berry extract to the human in need thereof, wherein the ginseng berry extract is obtained by extraction with 100% water, wherein ginsenoside Re is present in the highest amount among the ginsenosides in the ginseng berry extract, wherein syringaresinol is absent in the ginseng berry extract, and wherein the extract is configured to inhibit AE2 accumulation in retinal pigment epithelial cells, death of retinal pigment epithelial cells induced by blue light, or damage to an outer nuclear layer of visual cells in the human in need thereof.

2. The method of claim 1, wherein the ginseng berry extract is extracted from a *Panax* selected from a group consisting of *Panax ginseng, Panax quiquefolius, Panax notoginseng, Panax japonicus, Panax trifolium, Panax pseudoginseng, Panax vietnamensis, Panax quinquefolium* and mixtures thereof.

3. The method of claim 1, wherein the ginseng berry extract contains ginsenoside Re, Rc or Rd.

4. The method of claim 1, wherein the extract increases SIRT 1 (Sirtuin 1) expression and mitochondrial synthesis of retinal cells.

5. The method of claim 1, wherein the extract is a pharmaceutical composition, a food composition, or a health functional food composition.

* * * * *